US009946082B2

(12) United States Patent
Gerlitz

(10) Patent No.: US 9,946,082 B2
(45) Date of Patent: Apr. 17, 2018

(54) HANDHELD, LOW-LEVEL LASER APPARATUSES AND METHODS FOR LOW-LEVEL LASER BEAM PRODUCTION

(71) Applicant: Medical Coherence LLC, Fairfield, NJ (US)

(72) Inventor: Yonatan Gerlitz, Herzliya (IL)

(73) Assignee: Medical Coherence LLC, Fairfield, NJ (US)

( * ) Notice: Subject to any disclaimer, the term of this patent is extended or adjusted under 35 U.S.C. 154(b) by 173 days.

(21) Appl. No.: 14/963,511

(22) Filed: Dec. 9, 2015

(65) Prior Publication Data

US 2016/0085079 A1   Mar. 24, 2016

Related U.S. Application Data

(63) Continuation-in-part of application No. 13/873,602, filed on Apr. 30, 2013, now Pat. No. 9,553,422.
(Continued)

(51) Int. Cl.
*G02B 27/14* (2006.01)
*G02B 13/14* (2006.01)
(Continued)

(52) U.S. Cl.
CPC ........... *G02B 27/0955* (2013.01); *A61N 5/06* (2013.01); *A61N 5/0616* (2013.01);
(Continued)

(58) Field of Classification Search
USPC ................................. 359/629–637, 356, 357
See application file for complete search history.

(56) References Cited

U.S. PATENT DOCUMENTS 2,519,108 A   8/1950   Bryant et al.
2,761,224 A   9/1956   Gardiner
(Continued)

FOREIGN PATENT DOCUMENTS

CN       1901968 A    1/2007
CN    102573991 A    7/2012
(Continued)

OTHER PUBLICATIONS

International Preliminary Report on Patentability for International Application No. PCT/US2015/065079 dated Jun. 22, 2017.
(Continued)

*Primary Examiner* — Mohammed Hasan
(74) *Attorney, Agent, or Firm* — Parsons Behle & Latimer

(57) ABSTRACT

A handheld, low-level laser apparatus includes a laser diode configured to generate a laser emission having an astigmatism. The apparatus further includes one or more corrective lens configured alone or in combination to correct the astigmatism and to collimate the laser emission, a divergence lens configured to diverge the laser emission after the laser emission passes through the one or more corrective lens, and a front lens configured to collimate the laser emission after the laser emission passes through the divergence lens. A low-level laser beam producing method includes repeatedly directing an IR laser emission through a series of lenses during a first set of time periods and repeatedly directing a visible laser emission through the series of lenses during a second set of time periods, each time period of the first set of time periods being distinct from each time period of the second set of time periods.

21 Claims, 10 Drawing Sheets

Related U.S. Application Data

(60) Provisional application No. 62/090,307, filed on Dec. 10, 2014.

(51) Int. Cl.

| | | |
|---|---|---|
| G02B 27/09 | (2006.01) | |
| G02B 27/00 | (2006.01) | |
| G02B 27/30 | (2006.01) | |
| G02B 3/06 | (2006.01) | |
| G02B 7/14 | (2006.01) | |
| A61N 5/06 | (2006.01) | |
| B23K 26/00 | (2014.01) | |
| B23K 26/06 | (2014.01) | |
| B23K 26/70 | (2014.01) | |
| A61N 5/067 | (2006.01) | |
| A61B 18/20 | (2006.01) | |
| A61B 17/00 | (2006.01) | |
| A61B 18/00 | (2006.01) | |
| B23K 103/00 | (2006.01) | |

(52) U.S. Cl.
CPC ...... *B23K 26/0096* (2013.01); *B23K 26/0648* (2013.01); *B23K 26/702* (2015.10); *G02B 3/06* (2013.01); *G02B 7/14* (2013.01); *G02B 13/146* (2013.01); *G02B 27/0025* (2013.01); *G02B 27/141* (2013.01); *G02B 27/30* (2013.01); *A61B 18/203* (2013.01); *A61B 2017/00017* (2013.01); *A61B 2017/00747* (2013.01); *A61B 2018/00452* (2013.01); *A61B 2018/00636* (2013.01); *A61B 2018/00642* (2013.01); *A61B 2018/2025* (2013.01); *A61N 2005/067* (2013.01); *A61N 2005/0644* (2013.01); *A61N 2005/0651* (2013.01); *A61N 2005/0659* (2013.01); *B23K 2203/32* (2015.10)

(56) References Cited

U.S. PATENT DOCUMENTS

| | | | |
|---|---|---|---|
| 3,204,346 | A | 9/1965 | Lockard et al. |
| 3,878,626 | A | 4/1975 | Isman |
| 4,062,132 | A | 12/1977 | Klimaszewski |
| 4,538,895 | A | 9/1985 | Higgins et al. |
| 4,753,521 | A * | 6/1988 | Deserno ............... G02B 6/4206 359/663 |
| 4,979,180 | A | 12/1990 | Muncheryan |
| 5,029,788 | A | 7/1991 | Hoskinson et al. |
| 5,147,349 | A | 9/1992 | Johnosn et al. |
| 5,208,701 | A | 5/1993 | Maeda |
| 5,259,380 | A | 11/1993 | Mendes et al. |
| 5,272,716 | A | 12/1993 | Soltz et al. |
| 5,317,822 | A | 6/1994 | Johnson |
| 5,337,491 | A | 8/1994 | Mascotte |
| 5,339,543 | A | 8/1994 | Lin |
| 5,344,434 | A | 9/1994 | Talmore |
| 5,410,532 | A * | 4/1995 | Ono ...................... G01J 9/0215 250/201.5 |
| 5,464,436 | A | 11/1995 | Smith |
| 5,663,828 | A | 9/1997 | Knowles |
| 5,802,738 | A | 9/1998 | Ferniani |
| 5,872,354 | A | 2/1999 | Hanson |
| 5,896,684 | A | 4/1999 | Lin |
| 5,941,837 | A | 8/1999 | Amano et al. |
| 6,013,096 | A | 1/2000 | Tucek |
| 6,069,748 | A | 5/2000 | Bietry |
| 6,108,138 | A | 8/2000 | Ophey et al. |
| 6,267,779 | B1 | 7/2001 | Gerdes |
| 6,306,160 | B1 | 10/2001 | Nidetzky |
| 6,349,486 | B1 | 2/2002 | Lin |
| 6,358,272 | B1 | 3/2002 | Widen |
| 6,418,643 | B1 | 7/2002 | Yang |
| 6,612,719 | B2 | 9/2003 | Richardson et al. |
| 6,746,473 | B2 | 6/2004 | Shanks et al. |
| 6,909,551 | B1 * | 6/2005 | Liu ..................... G02B 27/0955 33/227 |
| 7,118,563 | B2 | 10/2006 | Weckwerth et al. |
| 7,315,421 | B2 * | 1/2008 | Fujihara ............ B23K 26/0604 257/E23.179 |
| 7,374,569 | B2 | 5/2008 | Whatcott et al. |
| 7,465,307 | B2 | 12/2008 | Connors et al. |
| 7,479,137 | B2 | 1/2009 | Yamazaki |
| 7,524,328 | B2 | 4/2009 | Connors et al. |
| 2002/0068926 | A1 | 6/2002 | Ota et al. |
| 2002/0173833 | A1 | 11/2002 | Korman et al. |
| 2003/0058916 | A1 | 3/2003 | Tanaka et al. |
| 2003/0170586 | A1 | 9/2003 | Cozean et al. |
| 2003/0233138 | A1 | 12/2003 | Spooner |
| 2004/0158301 | A1 | 8/2004 | Tucek et al. |
| 2005/0053106 | A1 | 3/2005 | Herron et al. |
| 2005/0131499 | A1 | 6/2005 | Shanks et al. |
| 2006/0095099 | A1 | 5/2006 | Shanks et al. |
| 2006/0129211 | A1 | 6/2006 | Canitano et al. |
| 2006/0206173 | A1 | 9/2006 | Gertner et al. |
| 2006/0206176 | A1 | 9/2006 | Shanks et al. |
| 2006/0224218 | A1 | 10/2006 | Tucek et al. |
| 2007/0121069 | A1 | 5/2007 | Andersen et al. |
| 2007/0185552 | A1 | 8/2007 | Masotti et al. |
| 2007/0198004 | A1 | 8/2007 | Altshuler et al. |
| 2008/0027518 | A1 | 1/2008 | Island et al. |
| 2008/0058783 | A1 | 3/2008 | Altshuler et al. |
| 2008/0077198 | A1 | 3/2008 | Webb et al. |
| 2008/0091179 | A1 | 4/2008 | Durkin et al. |
| 2008/0091249 | A1 | 4/2008 | Wang |
| 2008/0125835 | A1 | 5/2008 | Laurent |
| 2008/0215123 | A1 | 9/2008 | Maricle et al. |
| 2008/0310166 | A1 | 12/2008 | Chinniah et al. |
| 2009/0073824 | A1 | 3/2009 | Kurozuka et al. |
| 2009/0105791 | A1 | 4/2009 | McGinnis et al. |
| 2010/0053070 | A1 | 3/2010 | Tsai et al. |
| 2011/0032960 | A1 | 2/2011 | Gerlitz |
| 2013/0041431 | A1 | 2/2013 | Gerlitz et al. |
| 2013/0317571 | A1 | 11/2013 | Gerlitz |

FOREIGN PATENT DOCUMENTS

| | | |
|---|---|---|
| EP | 1210915 A2 | 6/2002 |
| JP | H0199576 | 4/1989 |
| JP | 2003066368 | 3/2003 |
| JP | 2004538108 | 12/2004 |
| JP | 2005518255 | 6/2005 |
| JP | 2006518610 | 8/2006 |

OTHER PUBLICATIONS

European Patent Office; Extended European Search Report for Application No. 14794429.2 dated Oct. 19, 2016.

European Patent Office; Supplementary Search Report for Application No. 14794429.2 dated Nov. 7, 2016.

International Searching Authority; International Search Report and Written Opinion for Application No. PCT/US2015/065079 dated Feb. 26, 2016.

US Patent and Trademark Office; Office Action for U.S. Appl. No. 14/963,511 dated Aug. 1, 2017.

US Patent and Trademark Office, Non-Final Office Action for U.S. Appl. No. 12/534,878 dated Jul. 12, 2012.

US Patent and Trademark Office, Non-Final Office Action for U.S. Appl. No. 12/534,878 dated Feb. 28, 2013.

US Patent and Trademark Office, Non-Final Office Action for U.S. Appl. No. 12/534,878 dated Jun. 17, 2013.

US Patent and Trademark Office, Final Office Action for U.S. Appl. No. 12/534,878 dated Jan. 6, 2014.

Japan Patent Office; Office Action for Japanese Patent Application No. 2012-523429 dated Jan. 13, 2015.

International Search Report And The Written Opinion of the International Search Authority for Application No. PCT/IB14/01638 dated Feb. 24, 2015.

US Patent and Trademark Office, Office Action for U.S. Appl. No. 14/341,153 dated May 19, 2015.

(56) References Cited

OTHER PUBLICATIONS

International Bureau; IPRP for Application No. PCT/IB2014/001638 dated Nov. 12, 2015.
US Patent and Trademark Office, Office Action for U.S. Appl. No. 13/873,602 dated Nov. 25, 2015.
International Search Report And The Written Opinion of the International Search Authority for Application No. PCT/US2015/065079 dated Feb. 26, 2016.
US Patent and Trademark Office, Office Action for U.S. Appl. No. 13/774,957 dated Mar. 23, 2016.
Korean Intellectual Property Office; Office Action for Serial No. 10-2012-7005632 dated Jul. 22, 2016.
Canadian Intellectual Property Office; Office Action for Application No. 2,769,837 dated Apr. 12, 2016.
The State Intellectual Property Office of China; First Office Action Application No. 201480030065.9 dated Jan. 16, 2017.
Canadian Intellectual Property Office; Office Action for Application No. 2,769,837 dated Apr. 11, 2017.

\* cited by examiner

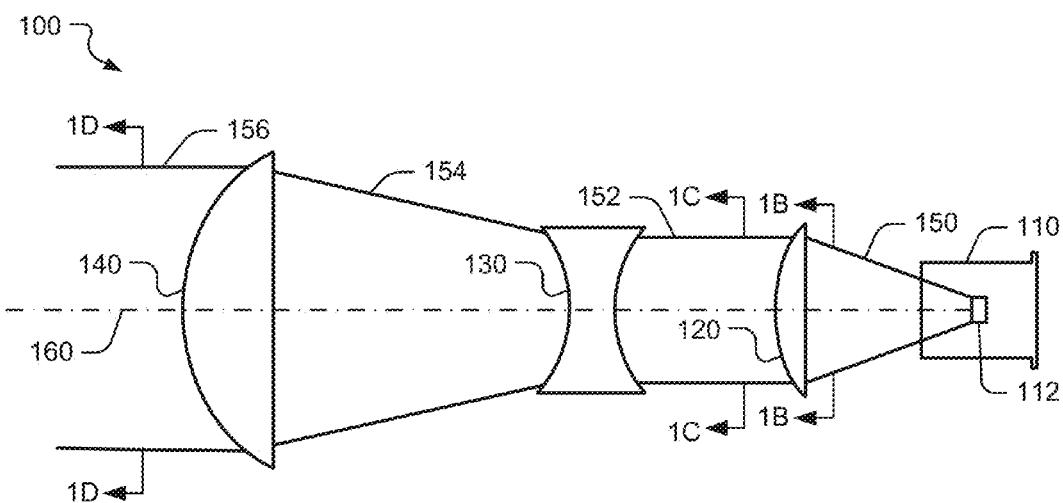
FIG. 1A
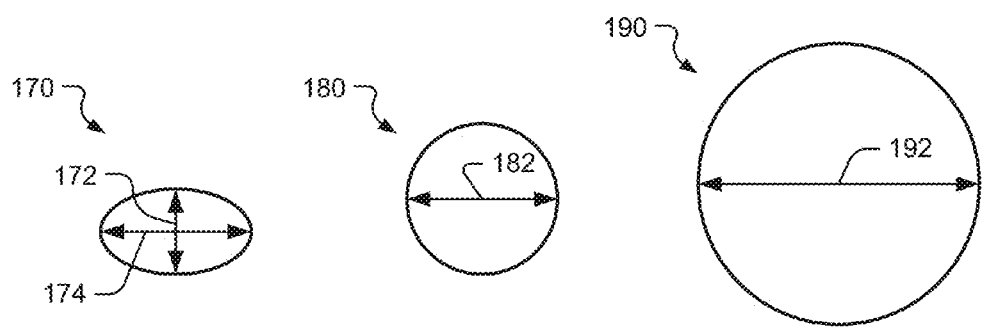
FIG. 1B  FIG. 1C  FIG. 1D

HANDHELD, LOW-LEVEL LASER APPARATUSES AND METHODS FOR LOW-LEVEL LASER BEAM PRODUCTION

CROSS REFERENCE TO RELATED APPLICATIONS

The present application claims the benefit of priority under 35 U.S.C. § 119 to U.S. Provisional App. No. 62/090,307, filed Dec. 10, 2014, entitled "Apparatus of Healing of Wounds". This application is a continuation-in-part of and claims priority to U.S. patent application Ser. No. 13/873,602 filed on Apr. 30, 2013 and entitled "Multiple Aperture Hand-Held Laser Therapy." Each of the indicated applications is incorporated herein by reference.

BACKGROUND

The present disclosure relates generally to the field of laser beam production, and more particularly to systems and methods for low-level laser beam production. Known low-level lasers produce a beam originating from the diode with an initial irradiance of about 5 mW/cm$^2$ (milliWatts/centimeter$^2$) to about 5 W/cm$^2$, such as 5 mW/cm$^2$ to about 1 W/cm$^2$. "Irradiance" refers to the power, or energy per time, per unit area of a laser emission. Irradiance might also be called "power density." Laser beams tend to have narrow cross sections. However, in some applications, particularly in the medical field, it may be beneficial to apply a laser beam over large areas.

Raw laser beams may lack coherence and/or may be too narrow to be effectively applied to a large area. Further, raw laser emissions may have high peak irradiance that may injure a person if directed into sensitive tissue such as an eye. As an additional drawback, particularly with respect to infrared (IR) laser beams, which are not humanly visible, it may be difficult to determine where the laser is pointing, increasing the risk of accidentally directing the laser into sensitive tissue.

SUMMARY

Methods and apparatuses are described herein that may overcome one or more of the deficiencies described above. One handheld, low-level laser apparatus includes a laser diode configured to generate an infrared (IR) laser emission propagating along a laser path. One or more corrective lens is positioned in the laser path and is configured to receive the IR laser emission therethrough. The one or more corrective lens is further configured alone or in combination to correct the astigmatism of the IR laser emission and to collimate the IR laser emission. A divergence lens is positioned in the laser path after the one or more corrective lens and is configured to receive the IR laser emission therethrough and to diverge the IR laser emission after the IR laser emission passes through the one or more corrective lens. A front lens is positioned in the laser path after the divergence lens and is configured to receive the IR laser emission therethrough and to collimate the IR laser emission after the IR laser emission passes through the divergence lens.

One low-level laser beam producing method includes, using a laser diode, generating an IR laser emission having an astigmatism and propagating the IR laser emission along a laser path. One or more corrective lens positioned in the laser path are used to receive the IR laser emission therethrough and, using the one or more corrective lens alone or in combination, to correct the astigmatism of the IR laser emission and collimate the IR laser emission. The method includes using a divergence lens positioned in the laser path after the one or more corrective lens, receiving the IR laser emission therethrough and diverging the IR laser emission after the IR laser emission passes through the one or more corrective lens. A front lens positioned in the laser path after the divergence lens receives the IR laser emission therethrough and collimates the IR laser emission after the IR laser emission passes through the divergence lens.

Another low-level laser beam producing method includes repeatedly directing an IR laser emission through a series of lenses during a first set of time periods. The method further includes repeatedly directing a visible laser emission through the series of lenses during a second set of time periods, each time period of the first set of time periods being distinct from each time period of the second set of time periods. In the method, the series of lenses increases collimation, which increases coherence, of a received laser emission corresponding to the IR laser emission, the visible laser emission, or both by collimating the received laser emission and correcting an astigmatism of the received laser emission, thereby forming a corrected laser emission. The series of lenses enlarges a cross section of the corrected laser emission, thereby forming an enlarged laser emission. The series of lenses also collimates the enlarged laser emission.

The features, functions, and benefits that have been discussed can be achieved independently in various embodiments or may be combined in yet other embodiments further details of which can be seen with reference to the following description and drawings.

BRIEF DESCRIPTION OF THE DRAWINGS

Some embodiments are described below with reference to the following accompanying drawings.

FIG. 1A depicts a low-level laser apparatus;

FIG. 1B depicts a cross-section of a raw laser emission;

FIG. 1C depicts a cross-section of the corrected laser emission 152;

FIG. 1D depicts a cross-section of the high-coherence laser emission 156;

DETAILED DESCRIPTION

Figure 2:
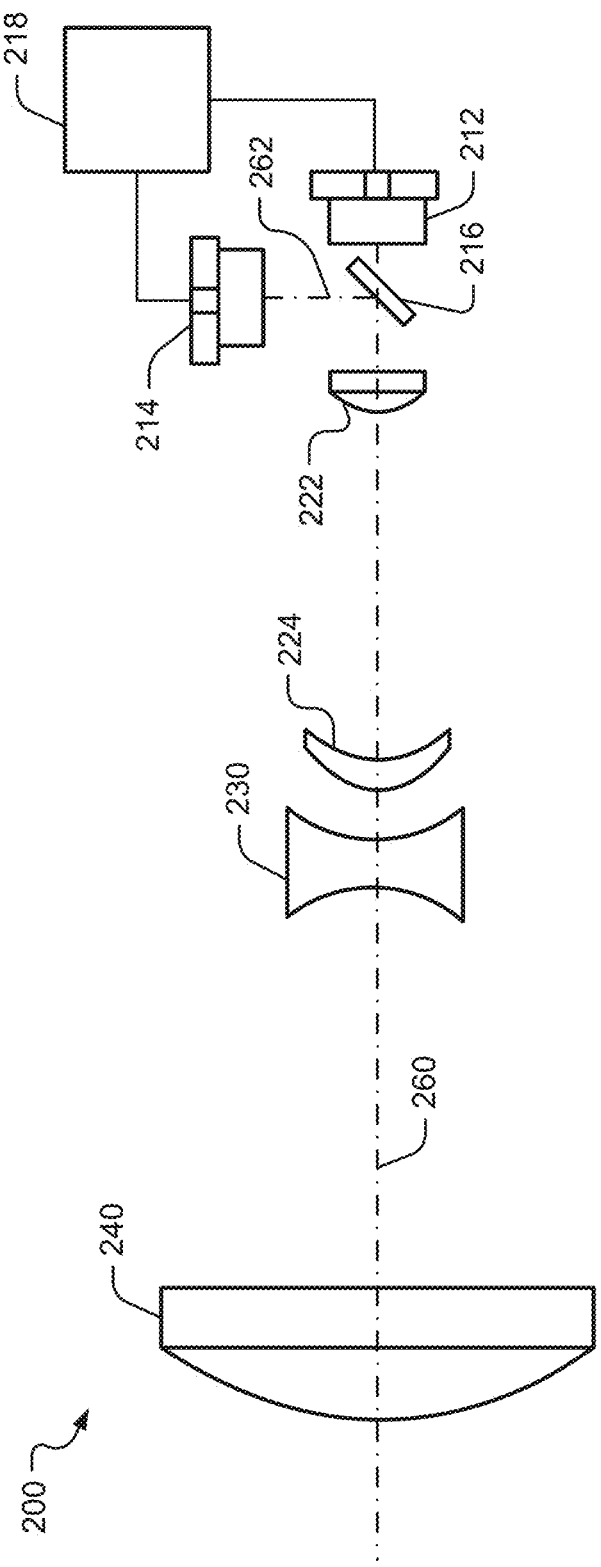
FIG. 2 depicts another low-level laser apparatus.

Referring to FIG. 1A, a low-level laser apparatus is depicted and generally designated 100. The apparatus 100 includes a laser source 110, a corrective lens 120, a divergence lens 130, and a front lens 140. Together, the corrective lens 120, the divergence lens 130, and the front lens 140 make up a series of lenses of an optical system that collimates in two stages and expands a cross-section of a laser beam between stages, thereby increasing the coherence of the laser beam.

The laser source 110 may include a laser diode 112. The laser diode 112 may be an infrared (IR) laser diode, such as a near-infrared (NIR) laser diode. For example, the laser diode 112 may be configured to generate a raw laser emission 150 in the IR region, such as in the NIR region (750 nm to 6,000 nm), of the electromagnetic spectrum. The raw laser emission 150 may have a wavelength from about 800 nm to about 850 nm. The exact wavelength range of the raw laser emission 150 may depend on manufacturing variation tolerances associated with the laser diode 112.

The raw laser emission 150 may be divergent due to a structure and configuration of the laser diode 112. For example, the laser diode 112 may lack lenses or deflectors to shape and guide the raw laser emission 150. The raw laser emission may include an astigmatism and may lack coherence, as described further with reference to FIG. 1B. The astigmatism may produce an emission that diverges with a small angle (e.g., from 5° to 7°) in one direction and with a larger angle (e.g., from 30° to 40°) in another perpendicular direction.

The raw laser emission 150 may propagate along a laser path 160 that passes through each of the series of lenses 120-140. For example, each of the lenses 120-140 may be aligned along the laser path 160 such that the raw laser emission 150 passes through each of the lenses 120-140.

The corrective lens 120 may be positioned in the laser path 160 between the laser diode 112 and the divergence lens 130, and may be configured to correct an astigmatism of the raw laser emission 150 and to collimate the raw laser emission 150, thereby forming a corrected laser emission 152. The corrective lens 120 may further be configured to correct the raw laser emission 150 by making the corrected laser emission 152 circular in cross-section. In order to correct the astigmatism and to perform the collimation, the corrective lens 120 may be a cylindrical or toroidal lens. The corrective lens 120 may further be aspherical, including an aspheric element reducing spherical or optical aberrations, to provide further correction and coherence to the raw laser emission 150. The apparatus 100 may also include a second corrective lens as described with reference to FIG. 2.

The divergence lens 130 may be configured to expand a cross-section of the corrected laser emission 152, thereby forming an expanding laser emission 154. The divergence lens 130 may further be configured to perform additional correction to the corrected laser emission 152. For example, the divergence lens 130 may be aspherical, including an aspheric element reducing spherical or optical aberrations, to adjust the corrected laser emission 152 to increase coherence.

The front lens 140 may be a collimating lens configured to collimate the expanding laser emission 154 to form a high-coherence laser emission 156. The extent to which the raw laser emission 150 is expanded may be based on a distance between the front lens 140 and the divergence lens 130. For example, a larger distance between the front lens 140 and the divergence lens 130 may result in a larger expansion of the raw laser emission 150 and a larger diameter of the high-coherence laser emission 156. Thus, the divergence lens 130 and the front lens 140, together, make a beam expander that increases the beam coherence of the corrected laser emission 152 in proportion to the beam expansion. The distance between the front lens 140 and the divergence lens 130 may be adjustable. As a non-limiting example, the front lens 140 may be included in a front lens assembly that is interchangeable with at least one other front lens assembly including another front lens, as described further with reference to FIGS. 5A-5C. The front lens 140 may be aspherical, including an aspheric element reducing spherical or optical aberrations, to perform additional correction to the expanding laser emission 154, and thereby increase a coherence of the high-coherence laser emission 156.

During operation, the laser diode 112 may generate the raw laser emission 150. The raw laser emission 150 may propagate along the laser path 160 and be received at the corrective lens 120. The corrective lens 120 may correct astigmatism of the raw laser emission 150 and collimate the raw laser emission 150 to form the corrected laser emission 152. The corrected laser emission 152 may be received at the divergence lens 130. The divergence lens 130 may expand a cross-section of the corrected laser emission 152 by forming the expanding laser emission 154. The expanding laser emission 154 may be received at the front lens 140. The front lens 140 may collimate the expanding laser emission 154 to form the high-coherence laser emission 156.

A benefit associated with the apparatus 100 is that an area of the high-coherence laser emission 156 may be larger as compared to low-level laser devices that do not expand laser emissions through a series of lenses such as the lenses 120-140. Due to the expansion, the high-coherence laser emission 156 may have better coherence compared to low-level laser devices that do not include two-stage collimation, such as two-stage collimation with beam expansion between stages. By first correcting and collimating and then diverging and collimating the raw laser emission 150 using the series of lenses 120-140, the apparatus 100 may produce high-coherence laser emissions (e.g., the high-coherence laser emission 156) that are significantly more collimated and coherent than unexpanded laser emissions.

For example, a coherence of the high-coherence laser emission 156 may increase as compared to unexpanded laser emissions by at least the same factor as the expansion. To illustrate, a 5× expansion may produce at least a 5× increase in coherence. The coherence may be further increased through the optical corrections made by the corrective lens 120 and/or by an aspheric shape of any of the series of lenses 120-140.

In applications where the apparatus 100 is used to apply a laser emission to a wound, the increased coherence of the high-coherence laser emission 156 may be more effective in increasing blood flow and/or stimulating healing than devices that do not use lenses to increase coherence. For example, applying the laser emission to a wound may increase vascular flexibility and/or reduce glycohemoglobin in the blood. The laser emission may thus be used to stimulate the healing of wounds, such as in the case of diabetic patients.

Another benefit associated with the apparatus 100 is that by expanding a cross-section of the raw laser emission 150 to produce the high-coherence laser emission 156, the high-coherence laser emission 156 may have a lower peak irradiance as compared to low-level laser devices that do not expand laser emissions after correction and collimation of raw laser emissions. The lower peak irradiance may reduce the risk of injury should the high-coherence laser emission 156 be inadvertently directed into someone's eye.

The high-coherence laser emission 156 may also have a more uniform irradiance distribution as compared to unexpanded laser emissions. The more uniform irradiance distribution may enable the laser emission to be applied more evenly over an application area. Specific irradiance distribution benefits are described further with reference to FIGS. 6-9. Other benefits of the apparatus 100 will be apparent to persons of ordinary skill in the art having the benefit of this disclosure.

Referring to FIG. 1B, an illustrated cross-section of the raw laser emission 150 is depicted and generally designated 170. The cross-section 170 may correspond to the indicated cross-section 1B of FIG. 1A and may be perpendicular to the laser path 160. Although FIG. 1B depicts the cross-section 170 as having a defined border, it should be understood that the cross-section 170 represents the shape of the irradiance distribution of the raw laser emission 150 and not a physical border of the raw laser emission 150. For example, the border of the ellipse of FIG. 1B may represent a sharp decline in the irradiance of the raw laser emission 150 as opposed to an absolute cutoff.

As depicted in FIG. 1B, the raw laser emission 150 may be a raw laser emission and may therefore be elliptical in shape. For example, the cross-section 170 may include a minor axis 172 and a major axis 174. Because the raw laser emission 150 expands, the length of the minor axis 172 and the major axis 174 may vary depending on the distance between the cross-section 170 and the laser diode 112. The elliptical shape of the cross-section 170 represents an astigmatism that occurs in the raw laser emission 150 as a result of the structure and generation process used by the laser diode 112.

Referring to FIG. 1C, an illustrated cross-section of the corrected laser emission 152 is depicted and generally designated 180. The cross-section 180 may correspond to the indicated cross-section 1C of FIG. 1A and may be perpendicular to the laser path 160. It should be understood that the cross-section 180 represents the shape of the irradiance distribution of the corrected laser emission 152. A diameter 182 of the cross-section 180 may be based on a shape and size of the corrective lens 120. The diameter 182 may further depend on a distance between the corrective lens 120 and the laser diode 112. A distance between the corrective lens 120 and the laser diode 112 may cause the diameter 182 to be about 8 mm. This may be an approximate value as the exact value of the diameter 182 may further depend on manufacturing variances associated with the corrective lens 120, the laser diode 112, or both.

Referring to FIG. 1D, an illustrated cross-section of the high-coherence laser emission 156 is depicted and generally designated 190. The cross-section 190 may correspond to the indicated cross-section 1D of FIG. 1A and may be perpendicular to the laser path 160. It should be understood that the cross-section 190 represents the shape of the irradiance distribution of the high-coherence laser emission 156. Because the high-coherence laser emission 156 has been enlarged and collimated by the divergence lens 130 and the front lens 140, a diameter 192 of the cross-section may be larger than the diameter 182 of the cross-section 180.

A value of the diameter 192 may depend on a distance between the front lens 140 and the divergence lens 130. For example, a greater distance between the front lens 140 and the divergence lens 130 may result in a greater value of the diameter 192. The diameter 192 may be chosen by selectively replacing the front lens 140 with another interchangeable lens at another distance from the divergence lens 130, as described with reference to FIGS. 5A-5B. To illustrate, the diameter 192 may be chosen by replacing the front lens 140 with a lens such that the cross-section 190 has an area of 2 cm$^2$, 4 cm$^2$, 6 cm$^2$, or another area.

As explained above, by expanding to a larger diameter, the high-coherence laser emission 156 may have better collimation and better coherence as compared to the raw laser emission 150 and/or the corrected laser emission 152. The expanded diameter 192 may further produce a lower peak irradiance and a more uniform irradiance distribution as compared to the cross-section 180 with the diameter 182.

Referring to FIG. 2, a low-level laser therapy apparatus is depicted and generally designated 200. The apparatus 200 includes a first laser diode 212, a second laser diode 214, and a dichroic combiner 216. The apparatus further includes a first corrective lens 222, a second corrective lens 224, a divergence lens 230, and a front lens 240, which together form a series of lenses 222-240 to expand a laser emission from either the first laser diode 212 or the second laser diode 214 to produce a high-coherence laser beam. Similar to the apparatus 100 of FIG. 1, the divergence lens 230 and the front lens 240, together, make a beam expander configured to increase the beam coherence of the corrected laser emission in proportion to the beam expansion. Accordingly, lenses 120-140 may also be used with the first laser diode 212, the second laser diode 214, and the dichroic combiner 216 in FIG. 2.

The first laser diode 212 may be configured to generate a first laser emission along a first laser path 260. The first laser diode 212 may be an IR or NIR laser diode configured to generate the first laser emission in the IR region or NIR region of the electromagnetic spectrum. The first laser emission may have a wavelength from about 800 nm to about 850 nm. The exact wavelength range of the first laser emission may depend on manufacturing variation tolerances associated with the first laser diode 212.

The second laser diode 214 may be configured to generate a second laser emission along a second laser path 262. The wavelength of the second laser emission may be in the visible portion of the electromagnetic spectrum. The second laser emission generated by the second laser diode 214 may have a wavelength from about 480 nm to about 530 nm. For example, the wavelength may correspond to the peak of the sun spectral radiance of approximately 480 nm. Instead, for example, the second laser diode 214 may be a green visible laser diode configured to generate the second laser emission in the green visible region of the electromagnetic spectrum, such as at a wavelength of approximately 525 nm. The exact wavelength may depend on manufacturing variation tolerances associated with the second laser diode 214. By corresponding to the peak of the sun spectral radiance or the green visible region, it is theorized that emissions from the second laser diode 214 may have a healing effect in applications where the apparatus 200 is used to apply a laser emission to a wound.

The dichroic combiner 216 may be configured to combine the first laser path 260 and the second laser path 262 by diverting the second laser path 262. For example, the dichroic combiner 216 may be reflective of the second laser emission generated by the second laser diode 214 and transparent to the first laser emission generated by the first laser diode 121. For example, the dichroic combiner may be reflective or transparent based on a wavelength of a laser emission received at the dichroic combiner. Further, the dichroic combiner 216 may be positioned at a meeting point of the first laser path 260 and the second laser path 262. An angle of the dichroic combiner 216 relative to the first laser path 260 and the second laser path 262 may cause the second laser emission to be reflected, such that the second laser path 262 is diverted along the first laser path 260. The first laser path 260 may remain undisturbed because the first laser emission passes through the dichroic combiner 216 without being reflected. Hence, both the first laser path 260 and the second laser path 262 may be directed through the series of lenses 222-240 along the same path.

The first laser diode 212 and the second laser diode 214 may be controlled by a controller 218. The controller may selectively activate the first laser diode 212 and the second laser diode 214. The controller may operate the laser diodes 212, 214 in a time-sharing duty cycle such that they are not simultaneously activated and only one of the first laser diode 212 and the second laser diode 214 is directed into the series of lenses 222-240 at a time so that no interference between the radiations occurs. The time-sharing duty cycle is described further with reference to FIG. 3. The controller may include a processor such as a central processing unit (CPU), a digital signal processor (DSP), a peripheral interface controller (PIC), another type of processing element, or a combination thereof. Alternatively or additionally, the controller may include an analog timing device or other circuitry capable of operating the laser diodes 212, 214 in a time-sharing duty cycle as described herein.

The first corrective lens 222 may be positioned in the laser path 260 between the dichroic combiner 216 and the second corrective lens 224, and may be configured to correct an astigmatism of a received laser emission, collimate the received laser emission, or both. In order to correct the astigmatism and/or to perform the collimation, the first corrective lens 222 may be a cylindrical or toroidal lens. The first corrective lens 222 may further be aspherical to provide further correction and coherence to a received laser emission. FIG. 2 shows first corrective lens 222 as a plano convex lens.

The second corrective lens 224 may be positioned in the laser path 260 between the first corrective lens 222 and the divergence lens 230, and may be configured to correct an astigmatism of a received laser emission, collimate the received laser emission, or both. As with the first corrective lens 222, in order to correct the astigmatism and to perform the collimation, the second corrective lens 224 may be a cylindrical or toroidal lens. The second corrective lens 224 may further be aspherical to provide further correction and coherence to a received laser emission. FIG. 2 shows second corrective lens 224 as a positive meniscus lens.

The first corrective lens 222 and the second corrective lens 224 may be configured together to correct an astigmatism of a received laser emission, collimate the received laser emission, or both. For example, the first corrective lens 222 may collimate a received laser emission and the second corrective lens 224 may correct an astigmatism of the received laser emission. Alternatively, the first corrective lens 222 may correct an astigmatism of the received laser emission and the second corrective lens 224 may collimate the received laser emission. The first and second corrective lenses 222, 224 may further be configured to correct a received raw laser emission for making a beam circular in cross-section. For example, the first corrective lens 222, the second corrective lens 224, or both, may be configured to change a shape of a received laser emission, thereby producing a circular beam for expansion. Such a beam may have a diameter of about 8 mm.

The divergence lens 230 may be configured to expand a cross-section of the corrected laser emission received from the second corrective lens 224, thereby forming an expanding laser emission. The divergence lens 230 may further be configured to perform additional correction to the corrected laser emission. For example, the divergence lens 230 may be aspherical to adjust the corrected laser emission to increase coherence. FIG. 2 shows divergence lens 230 as a biconcave lens.

The front lens 240 may be a collimating lens configured to collimate the expanding laser emission to form a high-coherence laser emission. The extent to which a laser emission is expanded may be based on a distance between the front lens 240 and the divergence lens 230. The distance between the front lens 240 and the divergence lens 230 may be adjustable. As a non-limiting example, the front lens 240 may be included in a front lens assembly that is interchangeable with at least one other front lens assembly including another front lens, as described further with reference to FIGS. 5A-5C. The front lens 240 may be aspherical to perform additional correction to the expanding laser emission, and thereby increase a coherence of the high-coherence laser emission. FIG. 2 shows front lens 240 as a plano convex lens.

During operation, a first laser emission may be repeatedly directed from the first laser diode 212 through the series of lenses 222-240 during a first set of time periods. A second laser emission may also be repeatedly directed from the second laser diode 214 through the series of lenses 222-240 during a second set of time periods. The first set of time periods may be distinct from each time period of the second set of time periods. Timing of the first laser emission and the second laser emission may be directed by the controller 218 within a time-sharing duty cycle to reduce or prevent interference between the first laser emission and the second laser emission.

The series of lenses 222-240, configured together, may collimate the received laser emission (e.g., either from the first laser diode 112 or the second laser diode 214) and correct an astigmatism of the received laser emission, thereby forming a corrected laser emission, as described herein. The series of lenses 222-240, when configured together, may also enlarge a cross section of the corrected laser emission, thereby forming an enlarged laser emission, and collimate the enlarged laser emission. In this way, the series of lenses 222-240 may collimate in two stages with expansion between stages and increase coherence of a received laser emission to generate a high-coherence laser emission.

A benefit associated with the apparatus 200 is that the second laser diode 214 may provide a visual indication of an area where an emission from the first laser diode 212 is being applied. Because the first laser diode 212 and the second laser diode 214 are operated at different times, a laser emission from the second laser diode 214 does not interfere with an emission from the first laser diode 212. Further, the visual indication may aid the user in seeing where the laser emission is being applied. Also, because the apparatus 200 gives a visual indication of where an emission of the first laser diode 212 is being applied, a user of the apparatus 200 may avoid inadvertently directing the laser emission in someone's eye.

In cases where the apparatus 200 may be used to stimulate the healing of lesions, another benefit includes the green laser emissions potentially being more effective than other portions of the visible electromagnetic spectrum in stimulating blood flow and/or healing. Wavelengths corresponding to the peak of the sun spectral radiance at around 480 nm may bear similar benefits. Hence, the apparatus 200 may be more effective at stimulating blood flow and/or healing than devices that do not use a visible laser emission.

Another benefit associated with the apparatus 200 is that an area of laser emission produced by the apparatus 200 may be larger as compared to low-level laser devices that do not expand laser emissions through a series of lenses, such as the lenses 222-240. Due to the expansion, the high-coherence laser emission may have better collimation and more coherence. Coherence of the high-coherence laser emission may be further increased through the optical corrections made by the corrective lenses 222, 224 and/or by an aspheric shape of any of the series of lenses 222-240.

By expanding a cross-section of the laser emissions from the laser diodes 212, 214, another benefit associated with the apparatus 200 includes the high-coherence laser emission having a lower peak irradiance as compared to low-level laser devices that do not expand laser emissions. Thereby, apparatus 200 reduces the risk of injury should the high-coherence laser emission be inadvertently directed into someone's eye. The high-coherence laser emission may also have a more uniform irradiance distribution as compared to unexpanded laser emissions, thereby enabling even application over an area. Other benefits of the apparatus 200 will be apparent to persons of ordinary skill in the art having the benefit of this disclosure.

Figure 3:
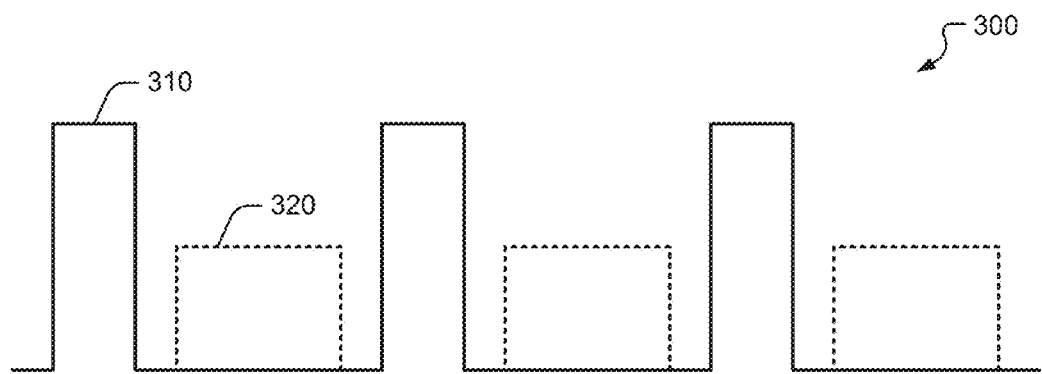
FIG. 3 depicts a timing diagram illustrating a time-sharing duty cycle for operating a first laser diode and a second laser diode.

Referring to FIG. 3, a timing diagram illustrating a time-sharing duty cycle for operating the first laser diode 212 and the second laser diode 214 is depicted and generally designated 300. A first function 310 indicates an operating time period corresponding to the first laser diode 212 and a second function 320 indicates an operating time period corresponding to the second laser diode 214. A power output produced by the laser diodes 212, 214 is depicted by the height of the functions 310, 320. For example, the first laser diode 212 may be operated at a higher power and for a shorter duration than the second laser diode 214. However, both may be operated at the same frequency, such as at 25 kHz. The first power output may be from 200 mW to 500 mW, such as 500 mW, and the second power output may be from 100 mW to 300 mW, such as 200 mW. The first laser diode 212 may be operated during 25% to 40%, such as 25%, of the time-sharing duty cycle and the second laser diode 214 may be operated during 25% to 50%, such as 50%, of the time-sharing duty cycle.

Figure 4:
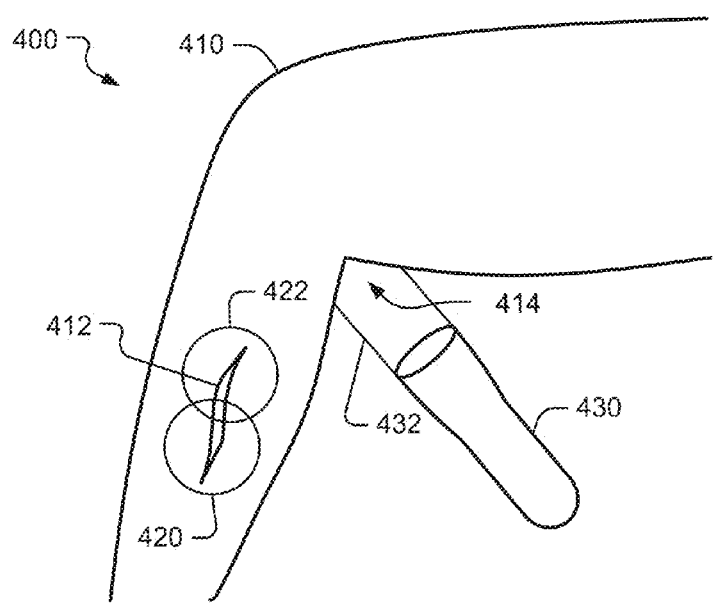
FIG. 4 depicts applying a low-level laser with increased coherence to an area.

Referring to FIG. 4, a diagram of applying a low-level laser with increased coherence to an area is depicted and generally designated 400. The area may be located on a patient's leg 410 and may include a wound 412. A handheld, low-level laser apparatus 430 includes the components of FIG. 2, producing a high coherence laser emission 432. Apparatus 430 may be handheld and thus sized to be capable of operating independent of an external support structure to hold the apparatus during use. Similarly, apparatus 430 may be capable of operating independent of an external power source. Despite the simplicity of its optical design and few optical components shown in FIG. 2, apparatus 430 nonetheless beneficially produces the high coherence laser emission 432 that might previously be produced only by bulkier or more complex devices that are not handheld and/or require an external power source.

Low-level laser apparatus 430 may be used for enhanced wound healing by daily irradiation of each area (e.g., a first area 422 and a second area 420) of the wound 412. Low-level laser apparatus 430 may be used for additional irradiation of the area of blood vessels supplying the wound area (e.g., behind the knee 414). For example, the high-coherence laser emission 432 may be applied to the first area 412 and the second area 420 for eight minutes each day and may be additionally applied behind the knee 414.

By applying the high-coherence laser emission 432 to the wound 412, blood flow to the wound 412 may be increased, thereby increasing a supply of oxygen to the cells in the area of the wound 412. The increase in blood flow may also provide greater capability for immune system cells to reach the wound 412 and increase potential for antibiotics to reach the wound 412.

Figure 5A:
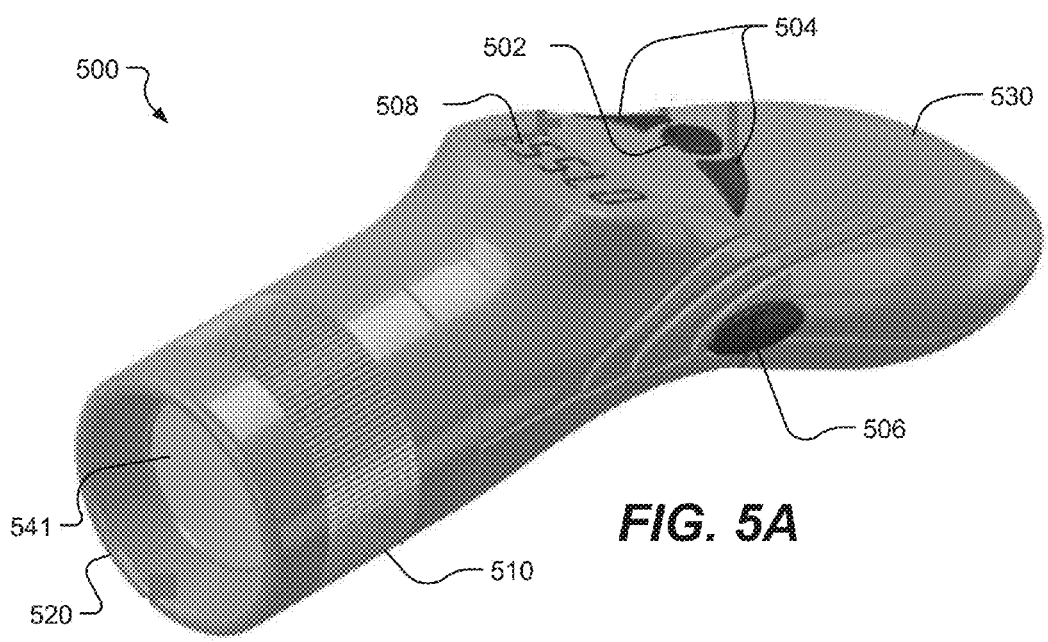
FIGS. 5A-5C depict a low-level laser apparatus with interchangeable front lens assemblies.
Figure 5B:
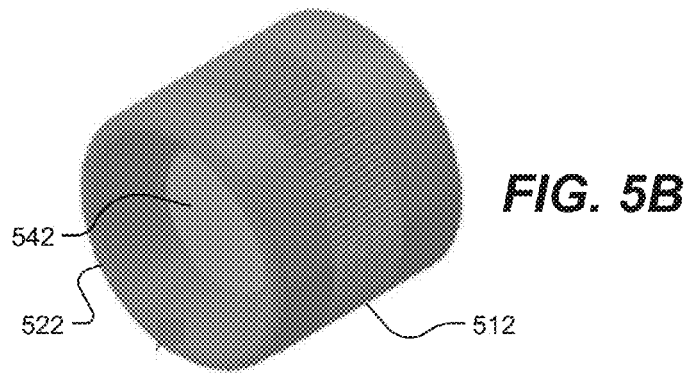

Referring to FIGS. 5A-5B, a low-level laser apparatus with interchangeable front lens assemblies is depicted and generally designated 500. The apparatus 500 may correspond to the apparatus 100 of FIG. 1, the apparatus 200 of FIG. 2, or another high-coherence low-level laser apparatus. For example, the apparatus 500 may include a base 530 that includes the laser diode 112, the corrective lens 120, and the divergence lens 130, configured as described with reference to FIG. 1. The apparatus 500 may further include a first front lens assembly 520 that includes the front lens 140. As another example, the base 530 may include the first laser diode 212, the second laser diode 214, the dichroic combiner 216, the first corrective lens 222, the second corrective lens 224, and the divergence lens 230, configured as described with reference to FIG. 2. In this example, the front lens assembly 520 may include the front lens 240.

The base 530 may provide a human interface for controlling functions of the apparatus 500. For example, the base 530 may include an on/off button 502 configured to enable selectively applying power to the apparatus 500. To illustrate, the on/off button 502 may be used to toggle a connection between components of the base 530 and a power supply (not shown). The power supply may include a power storage device, such as a battery. The base 530 may further include setup buttons 504. The setup buttons 504 may enable setting a timer for using the apparatus 500. For example, the timer may direct a time period for applying laser emissions from the apparatus 500 to an area. The base 530 may also include a start button 506. The start button may activate a laser emission from the apparatus 500 and start the timer. At the expiration of the timer, the laser emission may be terminated. An amount of time remaining at the timer and a subsequent countdown may be displayed at a display 508. The display 508 may include a liquid crystal diode (LCD) display, a light emitting diode (LED) display, another type of display, or a combination thereof. In addition to the timer, the display 508 may provide an indication of other user settings of the apparatus 500.

As depicted in FIG. 5A, a first front lens assembly 520 may be releasably coupled to the apparatus 500. For example, a bayonet mechanism 510, as is known for camera lenses, may be used to remove the front lens assembly 520 from the base 530 in order to switch to another front lens assembly. The first front lens assembly 520 may include a first front lens 541. The first front lens 541 may be a collimating lens as described with reference to FIGS. 1 and/or 2.

When the first front lens assembly 520 is coupled to the base 530, the first front lens 541 may be positioned in a laser path after a divergence lens to receive a laser emission therethrough after the laser emission passes through the divergence lens. A distance between the first front lens 541 and the divergence lens may be selected such that the apparatus 500 expands a cross-section of a laser emission to have an area of approximately 6 cm$^2$ after passing through the first front lens assembly 520.

As depicted in FIG. 5B, a second front lens assembly 522 may be configured to be releasably coupled to the base 530 interchangeably with the first front lens assembly 520. For example, the bayonet mechanism 510 may be used to remove the front lens assembly 520 from the base 530 and a second bayonet mechanism 512 may be used to releasably couple the second front lens assembly 522 to the base 530. The second front lens assembly 522 may include a second front lens 542. The second front lens 542 may also be a collimating lens as described with reference to FIGS. 1 and/or 2.

When the second front lens assembly 522 is coupled to the base 530, the second front lens 542 of the second front lens assembly 522 may be positioned in the laser path after the divergence lens. A distance between the second front lens 542 and the divergence lens when the second front lens is coupled to the base assembly may be different than a distance between the first front lens 541 of the first front lens assembly 520 and the divergence lens. For example, a distance between the second front lens 542 of the second front lens assembly 522 and the divergence lens may be selected such that the apparatus 500 expands a cross-section of a laser emission to have an area of approximately 4 cm$^2$ after passing through the second front lens assembly 522.

Figure 5C:
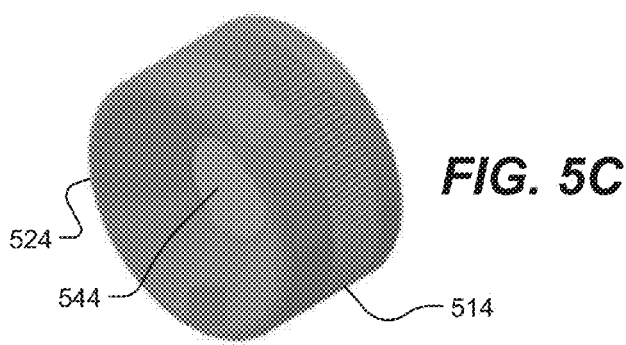

As depicted in FIG. 5C, a third front lens assembly 524 may be configured to be releasably coupled to the base 530 interchangeably with the first front lens assembly 520 and the second front lens assembly 522. For example, the bayonet mechanism 510 may be used to remove the first front lens assembly 520 from the base 530 or the bayonet mechanism 512 may be used to remove the second front lens assembly 522 from the base 530 and a third bayonet mechanism 514 may be used to releasably couple the third front lens assembly 524 to the base 530. The third front lens assembly 524 may include a third front lens 544. The third front lens 544 may also be a collimating lens as described with reference to FIGS. 1 and/or 2.

When the third front lens assembly 524 is coupled to the base 530, the third front lens 544 of the third front lens assembly 524 may be positioned in the laser path after the divergence lens. A distance between the third front lens 544 and the divergence lens when the third front lens is coupled to the base assembly 530 may be different than a distance between the first front lens 541 of the first front lens assembly 520 and the divergence lens and different than a distance between the second front lens 542 of the second lens assembly 522 and the divergence lens. For example, a distance between the third front lens 544 of the third front lens assembly 524 and the divergence lens may be selected such that the apparatus 500 expands a cross-section of a laser emission to have an area of approximately 2 cm$^2$ after passing through the third front lens assembly 524.

A benefit associated with the apparatus 500 is that a user may select an area of a high-coherence laser beam produced by the apparatus 500 dependent on a particular application. For example, a user may change a front lens assembly of the apparatus 500 to select a beam of 2 cm$^2$, 4 cm$^2$, or 6 cm$^2$. Further, when no front lens assembly is attached to the base 530, the resultant laser emission may not be collimated and therefore may continue to expand. As the laser emission expands, peak irradiance of the laser emission may decrease. Thus, peak irradiance of the laser emission may be decreased such that injury may be reduced or prevented if the laser emission is directed in someone's eye while no front lens assembly is coupled to the base 530. Other benefits of the apparatus 500 will be apparent to persons of ordinary skill in the art having the benefit of this disclosure. Although FIGS. 5A-5B depict three (3) front lens assemblies, the apparatus 500 may be configured to receive more or fewer than three (3) front lens assemblies interchangeably.

FIGS. 6-9, are irradiance distribution graphs of hypothetical beams irradiating a surface and showing optical performance for different levels of laser beam expansion. As a validation of the optical design shown in FIG. 2, the software that produced FIGS. 6-9 used one million rays of 808 nm wavelength irradiation originating from a source at varied directions and yielded less than 0.3° of divergence.

Figure 6:
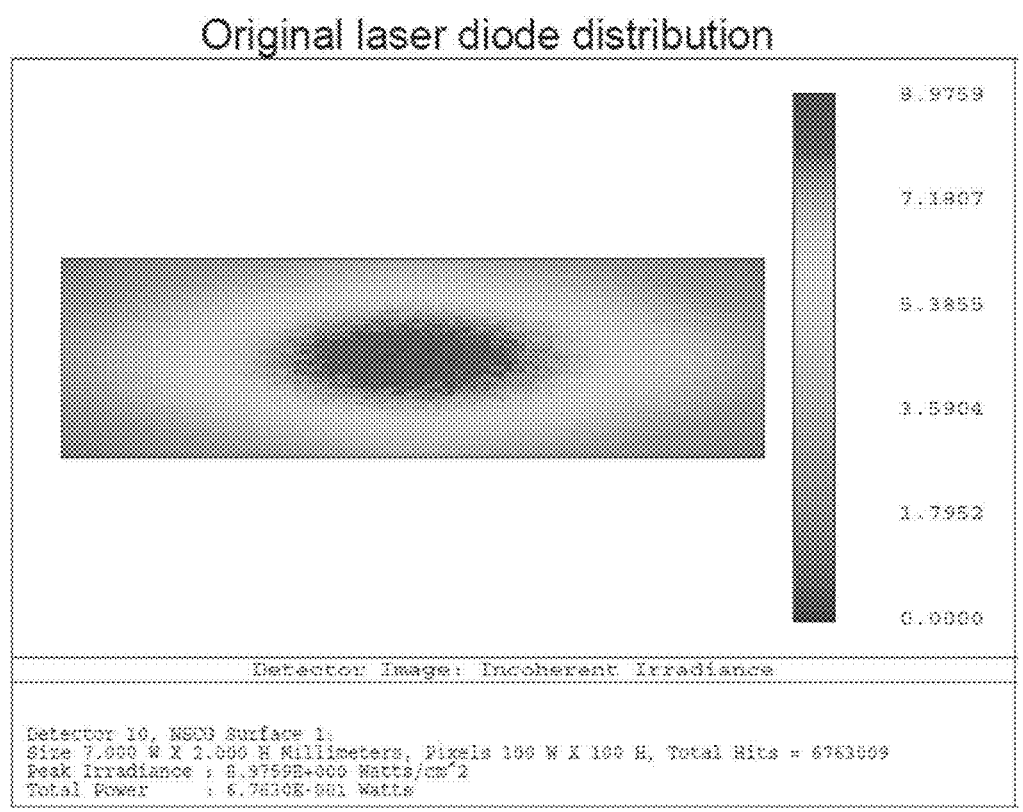
FIGS. 6-9 are irradiance distribution graphs in units of W/cm$^2$ showing optical performance for different levels of laser beam expansion.

Referring to FIG. 6, an irradiance distribution graph of an astigmatic laser emission irradiating a detector is shown. In FIG. 6, the laser emission has an elliptical shape. A major axis of the laser emission is 7 mm and a minor axis of the laser emission is 2 mm. Peak irradiance of the laser emission (depicted at the center of the graph) is approximately 8.9759 W/cm$^2$ and edge irradiance (depicted at a corner of the graph) is near 1.7952 W/cm$^2$. Total power of the detected radiation is 6.763×10$^{-1}$ W.

Figure 7:
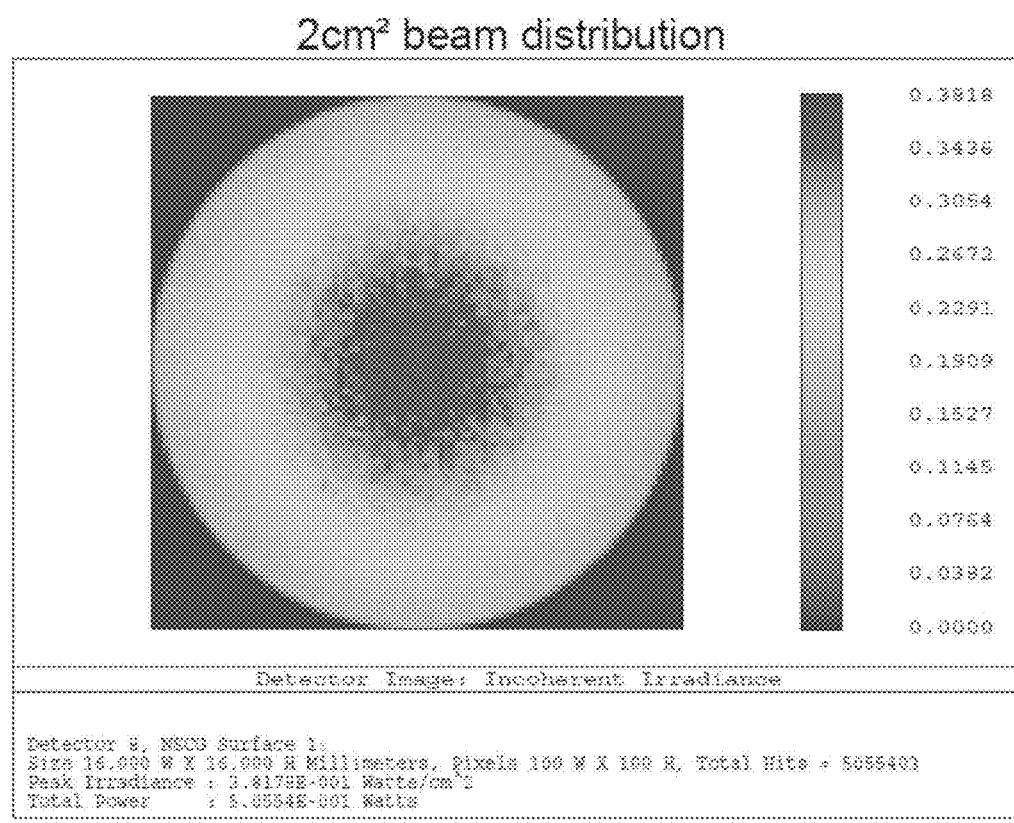

Referring to FIG. 7, an irradiance distribution graph of an expanded laser emission irradiating a detector is shown. The laser emission was modified by a beam expander to have a cross-sectional area of approximately 2 cm$^2$. The laser emission of FIG. 7 may correspond to laser emission from the front lens assembly 524 of FIG. 5. As shown in FIG. 7, the laser emission has a circular shape. A diameter of the laser emission is 16 mm. Peak irradiance of the laser emission (depicted at the center of the graph) is approximately 3.8178×10$^{-1}$ W/cm$^2$ and an edge irradiance (depicted a corner of the graph) is near zero W/cm$^2$. Thus, the irradiance distribution of the FIG. 7 laser emission is more uniform than the laser emission of FIG. 6. Further, peak irradiance of the laser emission of FIG. 7 is lower than peak irradiance of the laser emission of FIG. 6.

Figure 8:
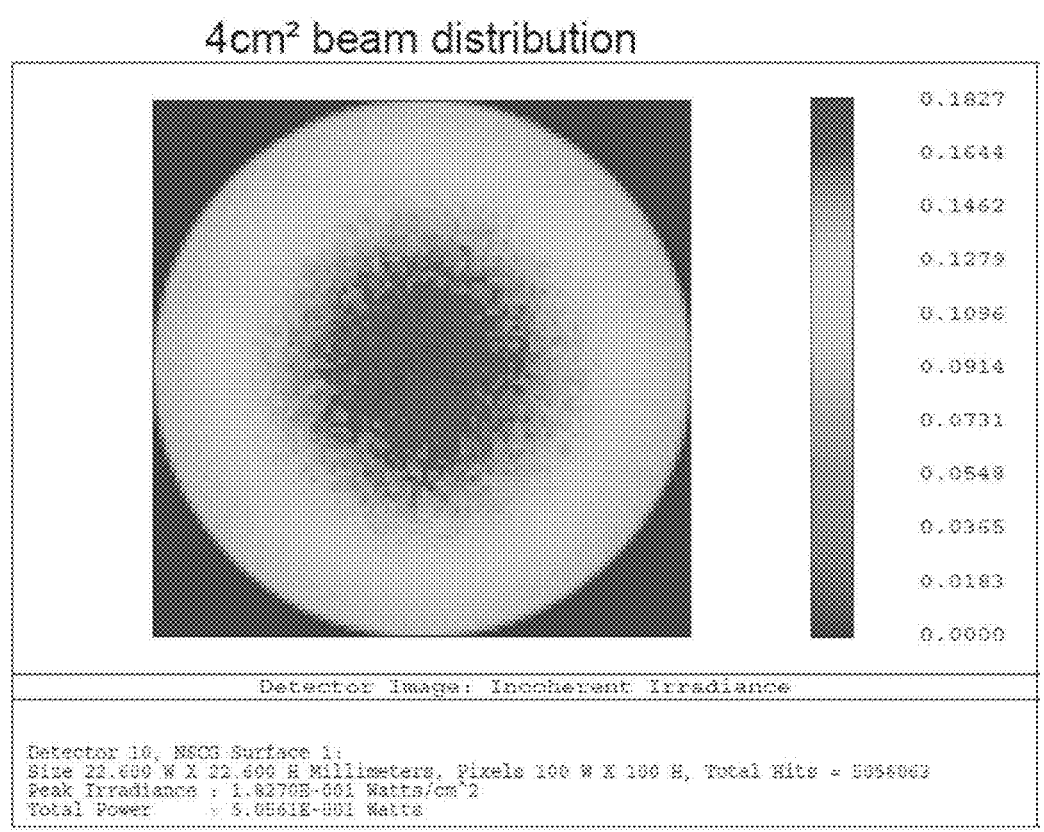

Referring to FIG. 8, an irradiance distribution graph of an expanded laser emission irradiating a detector is shown. The laser emission was modified by a beam expander to have a cross-sectional area of approximately 4 cm$^2$. The laser emission of FIG. 8 may correspond to laser emission from the front lens assembly 522 of FIG. 5. As shown in FIG. 8, the laser emission has a circular shape. A diameter of the laser emission is 22.6 mm. Peak irradiance of the laser emission (depicted at the center of the graph) is approximately 1.827×10$^{-1}$ W/cm$^2$ and an edge irradiance (depicted at a corner of the graph) is near zero W/cm$^2$. Thus, the irradiance distribution of the FIG. 8 laser emission is more uniform than the laser emissions of FIGS. 6 and 7. Further, peak irradiance of the laser emission of FIG. 8 is lower than peak irradiance of the laser emissions of FIGS. 6 and 7.

Figure 9:
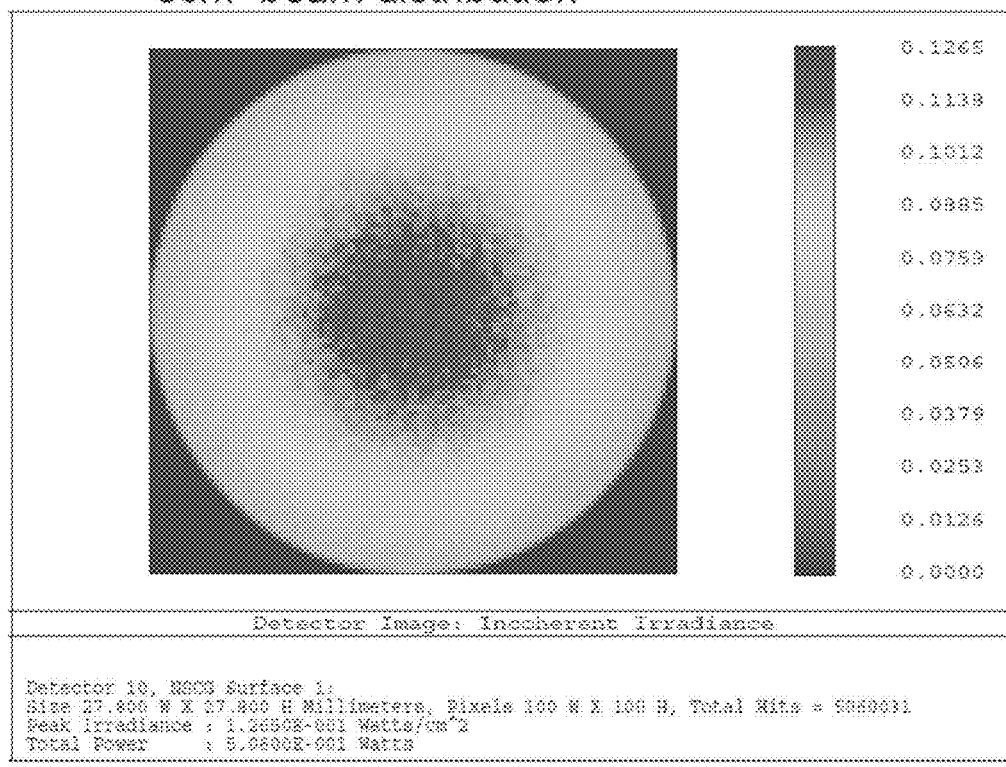

Referring to FIG. 9, an irradiance distribution graph of an expanded laser emission irradiating a detector is shown. The laser emission was modified by a beam expander to have a cross-sectional area of approximately 6 cm$^2$. The laser emission of FIG. 9 may correspond to laser emission from the front lens assembly 520 of FIG. 5. As shown in FIG. 9, the laser emission has a circular shape. A diameter of the laser emission is 27.8 mm. Peak irradiance of the laser emission (depicted at the center of the graph) is approximately 1.265×10$^{-1}$ W/cm$^2$ and an edge irradiance (depicted at a corner of the graph) is near zero W/cm$^2$. Thus, the irradiance distribution of the FIG. 9 laser emission is more uniform than the laser emission of FIGS. 6, 7, and 8. Further, peak irradiance of the laser emission of FIG. 9 is lower than peak irradiance of the laser emission of FIGS. 6, 7, and 8.

Thus, as shown in FIGS. 6-9, as a laser emission is modified by a beam expander, the irradiance distribution of the beam may become more uniform and better defined. Further, peak irradiance of the cross-section is reduced. Thus, the laser emission may be more evenly applied to an area and may present less risk of injury. Referring to the description of FIGS. 5A to 5C, it will be appreciated that the distance between the front lens 541, 542, 544 and the divergence lens may partly control peak irradiance exhibited by the laser emission after passing through the front lens.

Other benefits of the apparatuses and methods described herein will be apparent to persons of ordinary skill in the relevant art.

Figure 10:
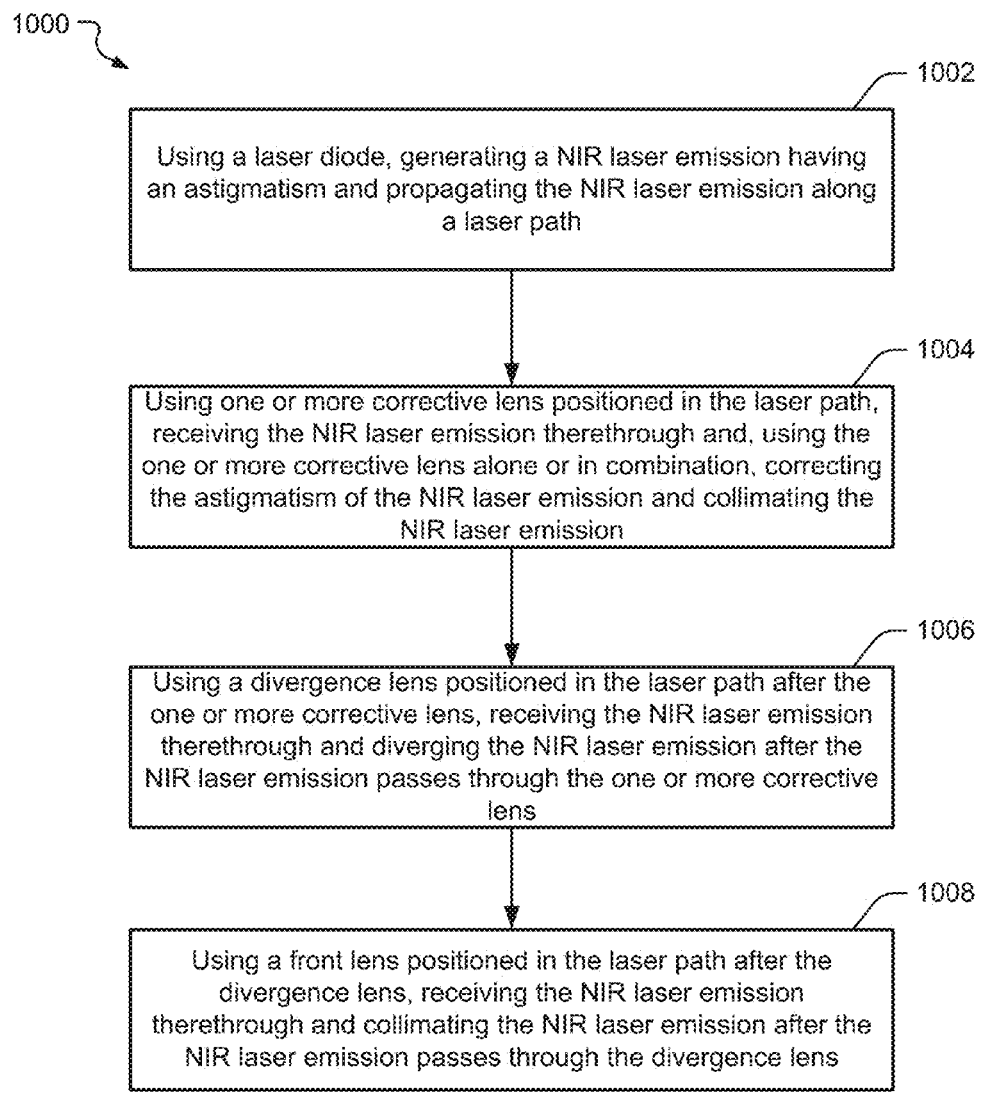
FIG. 10 is a flow chart of a low-level laser beam producing method.

Referring to FIG. 10, a flow chart of a low-level laser beam producing method is depicted and generally designated 1000. The method 1000 may include using a laser diode and generating a laser emission, at 1002. For example, the laser diode 112 may generate the raw laser emission 150.

The method 1000 may also include using a corrective lens positioned in the laser path and receiving the laser emission therethrough, at 1004. For example, the corrective lens 120 may receive the raw laser emission 150 therethrough.

The method 1000 may further include using a divergence lens positioned in the laser path and receiving the laser emission therethrough, at 1006. For example, the corrected laser emission 152 may be received through the divergence lens 130.

The method 1000 may include using a front lens positioned in the laser path after the divergence lens and receiving the laser emission therethrough after the laser emission passes through the divergence lens, at 1008. For example, the diverging laser emission 154 may be received at the front lens 140.

Figure 11:
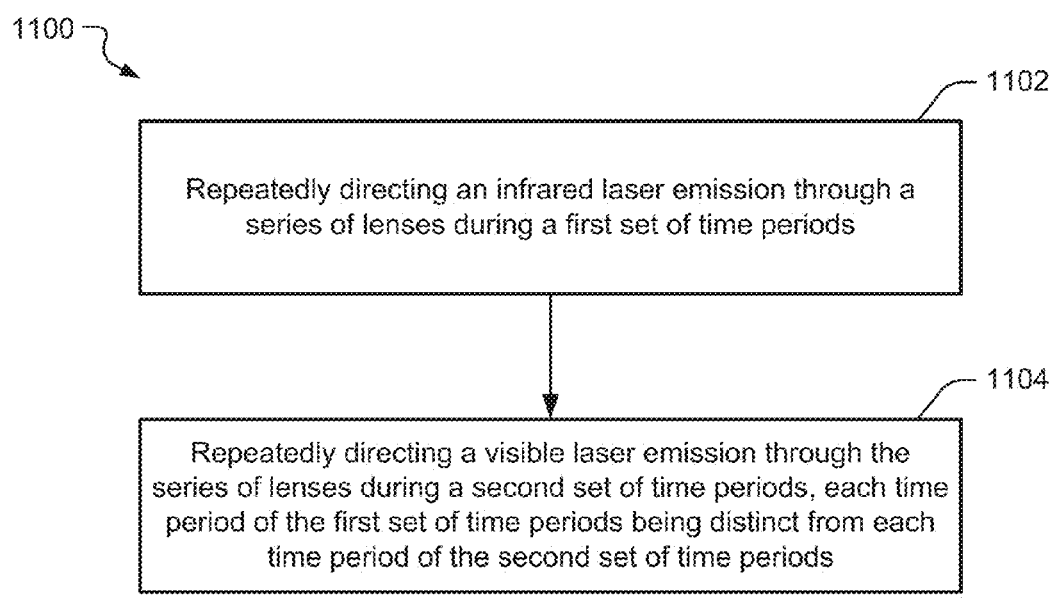
FIG. 11 is a flow chart of another low-level laser beam producing method.

Referring to FIG. 11, a flow chart of a low-level laser beam producing method is depicted and generally designated 1100. The method 1100 may include repeatedly directing an IR laser emission through a series of lenses during a first set of time periods, at 1102. For example, the first laser diode 212 may repeatedly direct an IR laser emission through the lenses 222-240.

The method 1100 may further include repeatedly directing a visible laser emission through the series of lenses during a second set of time periods, at 1104, each time period of the first set of time periods being distinct from each time period of the second set of time periods. For example, the second laser diode 214 may repeatedly direct a visible laser emission through the lenses 222-240.

In the method 1100, the series of lenses may increase a coherence of a received laser emission corresponding to the IR laser emission or the visible laser emission by collimating the received laser emission and correcting an astigmatism of the received laser emission, thereby forming a corrected laser emission. The series of lenses may further enlarge a cross section of the corrected laser emission, thereby forming an enlarged laser emission. The series of lenses may also collimate the enlarged laser emission.

In compliance with the statute, the embodiments have been described in language more or less specific as to structural and methodical features. It is to be understood, however, that the embodiments are not limited to the specific features shown and described. The embodiments are, therefore, claimed in any of their forms or modifications within the proper scope of the appended claims appropriately interpreted.

What is claimed is:

1. A handheld, low-level laser apparatus comprising:
   a laser diode configured to generate a near infrared (NIR) laser emission having an astigmatism and propagating along a laser path;
   one or more corrective lens positioned in the laser path and configured to receive the NIR laser emission therethrough, the one or more corrective lens being further configured alone or in combination to correct the astigmatism of the NIR laser emission and to collimate the NIR laser emission;
   a divergence lens positioned in the laser path after the one or more corrective lens and configured to receive the NIR laser emission therethrough and to diverge the NIR laser emission after the NIR laser emission passes through the one or more corrective lens; and
   a front lens positioned in the laser path after the divergence lens and configured to receive the NIR laser emission therethrough and to collimate the NIR laser emission after the NIR laser emission passes through the divergence lens.

2. A handheld, low-level laser apparatus comprising:
   a laser diode configured to generate a near infrared (NIR) laser emission having an astigmatism and propagating along a laser path;
   one or more corrective lens positioned in the laser path and configured to receive the NIR laser emission therethrough, the one or more corrective lens being further configured alone or in combination to correct the astigmatism of the NIR laser emission and to collimate the NIR laser emission;
   a divergence lens positioned in the laser path after the one or more corrective lens and configured to receive the NIR laser emission therethrough and to diverge the NIR laser emission after the NIR laser emission passes through the one or more corrective lens;
   a front lens positioned in the laser path after the divergence lens and configured to receive the NIR laser emission therethrough and to collimate the NIR laser emission after the NIR laser emission passes through the divergence lens; and
   another laser diode, the other laser diode being configured to generate a visible laser emission having an astigmatism and propagating along another laser path, the one or more corrective lens, the divergence lens, and the front lens being configured to receive the visible laser emission therethrough.

3. The apparatus of claim 2, further comprising a dichroic combiner positioned in the laser path and in the other laser path, the dichroic combiner being configured to combine the laser path and the other laser path into the same path by diverting a propagation direction of either the NIR or visible laser emission.

4. The apparatus of claim 2, wherein the NIR laser emission has a wavelength from 800 nm to 850 nm and the visible laser emission has a wavelength from 480 nm to 530 nm.

5. The apparatus of claim 2, further comprising a controller programmed to activate the laser diode and the other laser diode in a time-sharing duty cycle such that they are not simultaneously activated.

6. The apparatus of claim 1, wherein the one or more corrective lens is a cylindrical lens or a toroidal lens.

7. The apparatus of claim 1, wherein the one or more corrective lens is two corrective lenses configured together to correct the astigmatism of the laser emission and to collimate the laser emission.

8. The apparatus of claim 7, wherein the two corrective lenses are configured together to yield the laser emission with a substantially circular cross-section.

9. The apparatus of claim 8, wherein the circular cross-section has a diameter of approximately 8 mm.

10. The apparatus of claim 1, wherein the one or more corrective lens, the divergence lens, and the front lens are aspherical.

11. The apparatus of claim 1, wherein the apparatus is configured such that a distance between the front lens and the divergence lens partly controls peak irradiance exhibited by the laser emission after passing through the front lens.

12. A handheld, low-level laser apparatus comprising:
a laser diode configured to generate a near infrared (NIR) laser emission having an astigmatism and propagating along a laser path;
one or more corrective lens positioned in the laser path and configured to receive the NIR laser emission therethrough, the one or more corrective lens being further configured alone or in combination to correct the astigmatism of the NIR laser emission and to collimate the NIR laser emission;
a divergence lens positioned in the laser path after the one or more corrective lens and configured to receive the NIR laser emission therethrough and to diverge the NIR laser emission after the NIR laser emission passes through the one or more corrective lens;
a front lens positioned in the laser path after the divergence lens and configured to receive the NIR laser emission therethrough and to collimate the NIR laser emission after the NIR laser emission passes through the divergence lens;
a base assembly including the laser diode, the one or more corrective lens, and the divergence lens; and
a front lens assembly including the front lens and being configured to couple releasably to the base assembly to provide the front lens positioned in the laser path.

13. The apparatus of claim 12, further comprising a second front lens assembly configured to couple releasably to the base assembly interchangeably with the front lens assembly, the second front lens assembly including a second front lens positioned in the laser path after the divergence lens when the second front lens assembly is coupled to the base assembly, a distance between the second front lens and the divergence lens when the second front lens is coupled to the base assembly being different than a distance between the front lens and the divergence lens when the front lens assembly is coupled to the base assembly.

14. The apparatus of claim 13, further comprising a third front lens assembly configured to couple releasably to the base assembly interchangeably with the front lens assembly and the second front lens assembly, the third front lens assembly including a third front lens positioned in the laser path after the divergence lens when the third front lens assembly is coupled to the base assembly, a distance between the third front lens and the divergence lens when the third front lens is coupled to the base assembly being different than both a distance between the front lens and the divergence lens when the front lens assembly is coupled to the base assembly and a distance between the second front lens and the divergence lens when the second front lens assembly is coupled to the base assembly.

15. The apparatus of claim 14, a cross-section of the laser emission having an area of approximately 2 cm2 after passing through the front lens assembly, the cross-section of the laser emission having an area of approximately 4 cm2 after passing through the second front lens assembly, and the cross-section of the laser emission having an area of approximately 6 cm2 after passing through the third front lens assembly.

16. A low-level laser beam producing method comprising:
using a laser diode, generating a near infrared (NIR) laser emission having an astigmatism and propagating the NIR laser emission along a laser path;
using one or more corrective lens positioned in the laser path, receiving the NIR laser emission therethrough and, using the one or more corrective lens alone or in combination, correcting the astigmatism of the NIR laser emission and collimating the NIR laser emission;
using a divergence lens positioned in the laser path after the one or more corrective lens, receiving the NIR laser emission therethrough and diverging the NIR laser emission after the NIR laser emission passes through the one or more corrective lens; and
using a front lens positioned in the laser path after the divergence lens, receiving the NIR laser emission therethrough and collimating the NIR laser emission after the NIR laser emission passes through the divergence lens.

17. A low-level laser beam producing method comprising:
repeatedly directing a near infrared (NIR) laser emission through a series of lenses during a first set of time periods; and
repeatedly directing a visible laser emission through the series of lenses during a second set of time periods, each time period of the first set of time periods being distinct from each time period of the second set of time periods,
the series of lenses increasing the collimation, which increases the coherence, of a received laser emission corresponding to the NIR laser emission, the visible laser emission, or both by:
collimating the received laser emission and correcting an astigmatism of the received laser emission, thereby forming a corrected laser emission;
enlarging a cross section of the corrected laser emission, thereby forming an enlarged laser emission; and
collimating the enlarged laser emission.

18. The method of claim 17, wherein the NIR laser emission has a wavelength from 800 nm to 850 nm and the visible laser emission has a wavelength from 480 nm to 530 nm.

19. The method of claim 17, wherein the first set of time periods and the second set of time periods correspond to a time-sharing duty cycle.

20. The method of claim 19, wherein repeatedly directing the NIR laser emission through the series of lenses is performed during 25% to 40% of the time-sharing duty cycle, and wherein repeatedly directing the visible laser emission through the series of lenses is performed during 25% to 50% of the time-sharing duty cycle.

21. The method of claim 17, further comprising synchronizing the first set of time periods and the second set of time periods using a processor.

* * * * *